(12) United States Patent
Crainich et al.

(10) Patent No.: US 6,293,956 B1
(45) Date of Patent: Sep. 25, 2001

(54) LIGATING CLIPS

(75) Inventors: Lawrence Crainich, Charlestown; Alfred C. Loiselle, III, South Acworth, both of NH (US)

(73) Assignee: Designs Standards Corporation, Charlestown, NH (US)

( * ) Notice: Subject to any disclaimer, the term of this patent is extended or adjusted under 35 U.S.C. 154(b) by 0 days.

(21) Appl. No.: 09/491,128

(22) Filed: Jan. 26, 2000

(51) Int. Cl.$^7$ .................................................. A61B 17/122
(52) U.S. Cl. ............................................ 606/155; 606/151
(58) Field of Search ..................................... 606/142, 143, 606/151, 157, 158, 72, 75, 213, 219, 221, 155

(56) References Cited

U.S. PATENT DOCUMENTS

| | | | |
|---|---|---|---|
| 5,593,414 | * | 1/1997 | Shipp et al. ........................ 606/142 |
| 5,758,420 | * | 6/1998 | Schmidt et al. .................... 29/896.9 |
| 5,766,189 | * | 6/1998 | Matsuno ............................. 606/158 |

* cited by examiner

*Primary Examiner*—David O. Reip
(74) *Attorney, Agent, or Firm*—Bachman & LaPointe, P.C.

(57) ABSTRACT

A ligating clip includes a first leg and a second leg defining therebetween a tissue clamping zone; and a deformable head portion connecting the first leg and the second leg and deformable from an open position wherein the first leg and the second leg are spaced to receive tissue to a closed position wherein the first leg and the second leg are closed to clamp tissue, wherein the deformable head portion defines deforming force receiving surfaces which are outside the tissue clamping zone.

13 Claims, 6 Drawing Sheets

LIGATING CLIPS

BACKGROUND OF THE INVENTION

The invention relates to ligating clips and, more particularly, to a structure and method for more securely and safely applying same.

Ligating clips are in wide use in the surgical field. Such clips are conventionally used for clamping tissues as needed during various procedures. A basic conventional ligating clip C is illustrated in FIG. 1, and is a simple U or V-shaped structure clamped onto tissue T so as to ligate same.

Figure 1:
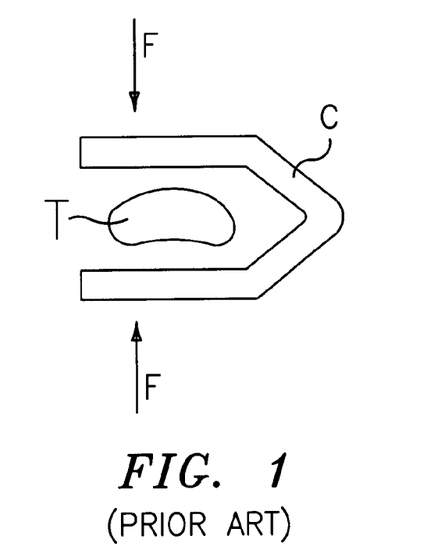
FIG. 1 illustrates a prior art clip.

In application, a pliers or other device is typically used to apply force as shown by the arrows in FIG. 1 so as to deform or crimp the clip around the tissue as desired. During such application, as is readily apparent from FIG. 1, the clip closing force is directed at components of the clip which are themselves in direct contact with the tissue. Thus, the greater force applied to the clip, the greater will be the force transmitted to the tissue, and application of too great of a force can cause damage to the tissue.

Clearly, the need remains for a simple and effective clip which can reliably and securely be applied to tissue for safe and effective clamping or ligation of same.

It is therefore the primary object of the present invention to provide a clip which is safe in application.

It is a further object of the present invention to provide a clip which is readily manipulated and positioned for use.

It is a still further object of the present invention to provide a clip which is simple and efficient in manufacture.

It is another object of the present invention to provide a method for applying clips which is safe and effective.

It is still another object of the present invention to provide a clip and method whereby a smaller diameter device can advantageously be used to apply the clip.

Other objects and advantages of the present invention will appear hereinbelow.

SUMMARY OF THE INVENTION

In accordance with the present invention, the foregoing objects and advantages have been readily attained.

In accordance with the invention, a ligating clip is provided which comprises a first leg and a second leg defining therebetween a tissue clamping zone; and a deformable head portion connecting said first leg and said second leg and deformable from an open position wherein said first leg and said second leg are spaced to receive tissue to a closed position wherein said first leg and said second leg are closed to clamp tissue, wherein said deformable head portion defines deforming force receiving surfaces which are outside said tissue clamping zone.

Embodiments of clips having U, O, W and T-shaped head portions are disclosed. Further, a method for applying such clips whereby clip deforming or applying force is applied outside of the clip clamping zone is provided. This further allows the use of a smaller size or diameter device to apply the clip.

BRIEF DESCRIPTION OF THE DRAWINGS

A detailed description of preferred embodiments of the invention follows, with reference to the attached drawings, wherein.

DETAILED DESCRIPTION

The invention relates to surgical or ligating clips for use in clamping or clipping various tissues such as blood vessels and the like.

Figure 2:
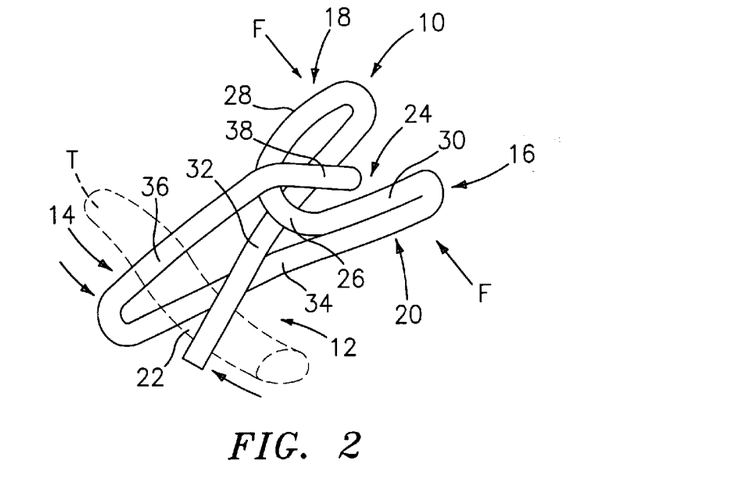
FIGS. 2–5 illustrate a clip in accordance with the present invention having a U-shaped head portion.

FIG. 2 illustrates one embodiment of a clip 10 in accordance with the invention. Clip 10 according to the invention includes a first leg 12 and a second leg 14, and a deformable head portion 16 for connecting first leg 12 and second leg 14. Clip 10 in accordance with the present invention is said to be a deformable clip in that the clip is provided preferably in an open position as illustrated in FIG. 2, and is crimped or deformed during application into a closed position. Head portion 16 in accordance with the present invention advantageously defines deforming force receiving surfaces 18, 20, while first leg 12 and second leg 14 define a tissue clamping zone 22 for clamping tissue T as desired.

In accordance with the present invention, and advantageously, deforming force receiving surfaces 18, 20 are positioned outside of tissue clamping zone 22 such that application of force to surfaces 18, 20 does not result in direct application of force to tissue T as with conventional ligating clips (see, for example, FIG. 1). Rather, application of deforming force to surfaces 18, 20 results in pivot of first leg 12 and second leg 14 relative to each other into closed position for clamping tissue T as desired.

As will be further explained below, this structure completely avoids the possibility of application of excessive force to tissue T through application of excessive force to close the clip as can happen with conventional clips. Rather, the location of deforming force receiving surfaces 18, 20 outside of tissue clamping zone 22 results in a maximum possible force that can be applied to tissue T which is substantially the same as the yield strength of the material from which clip 10 is manufactured. This is particularly advantageous in connection with deformable clips wherein force must be applied to close same.

Figure 3:
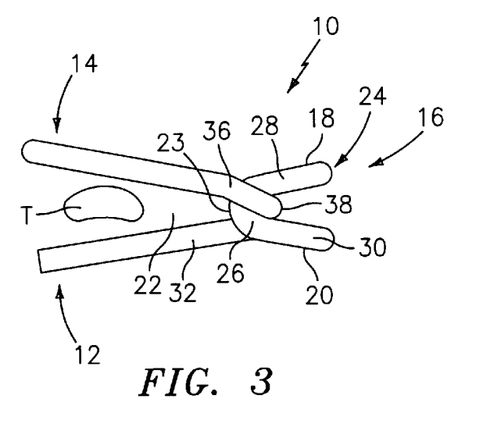
Figure 4:
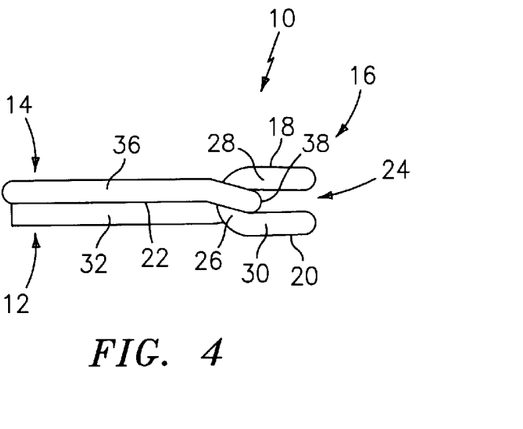
Figure 5:
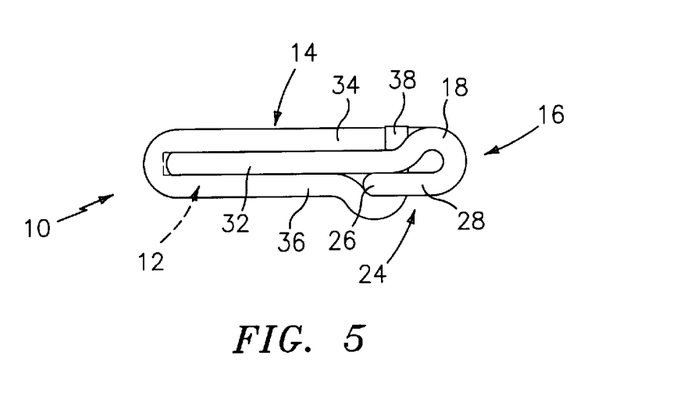
Figure 6:
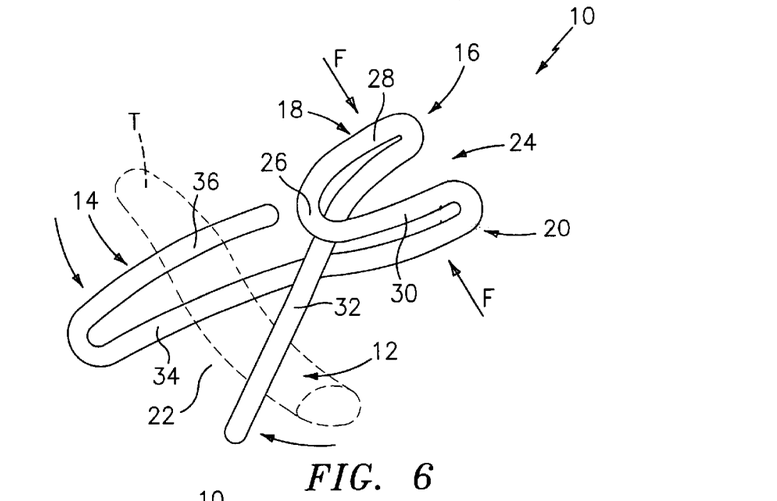
FIGS. 6–9 illustrate an alternative embodiment of the clip of the present invention having a U-shaped head portion.
Figure 7:
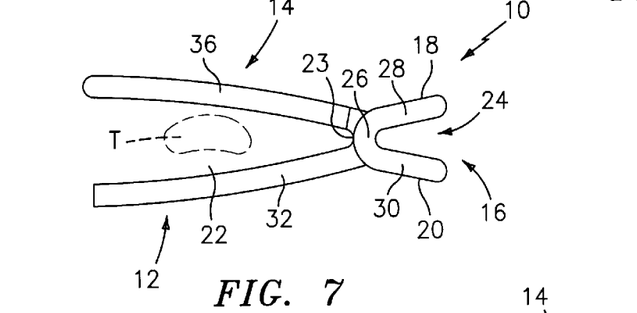
Figure 8:
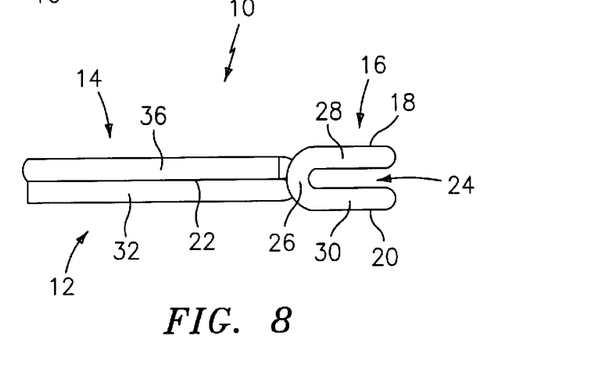
Figure 9:
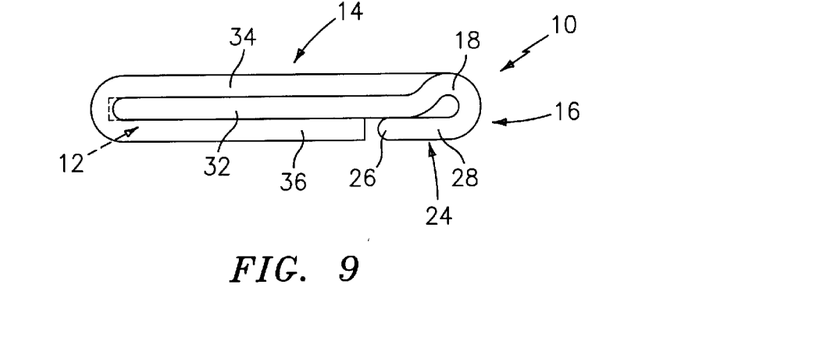
Figure 10:
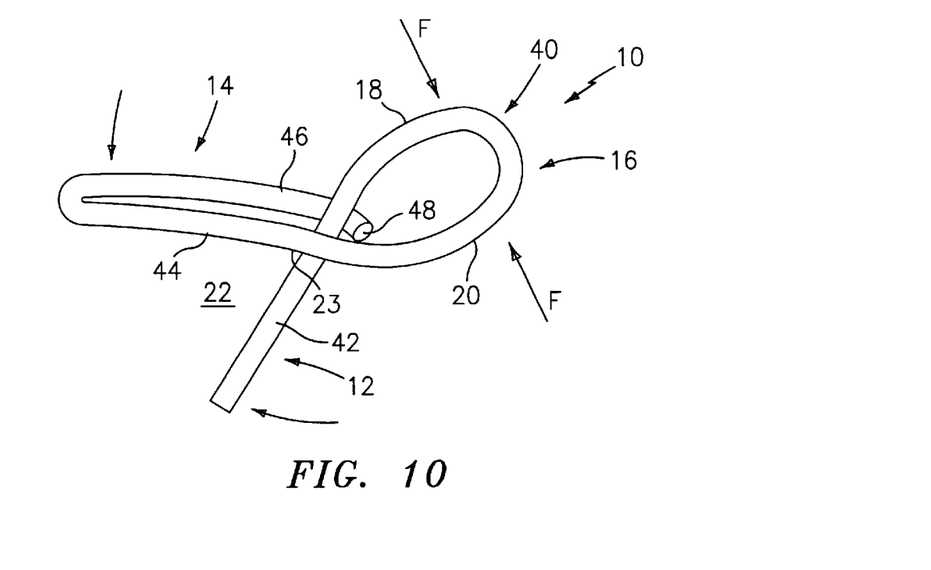
FIGS. 10–13 illustrate a clip in accordance with the present invention having an O-shaped head portion.
Figure 11:
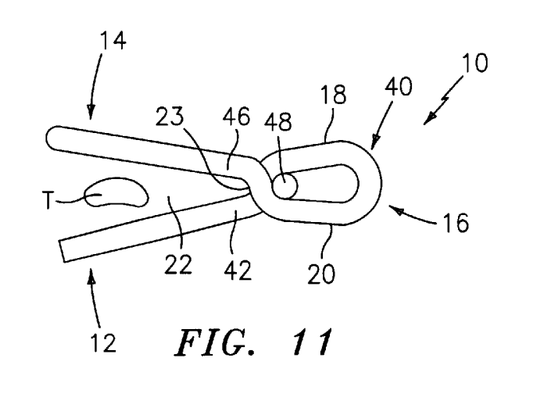
Figure 12:
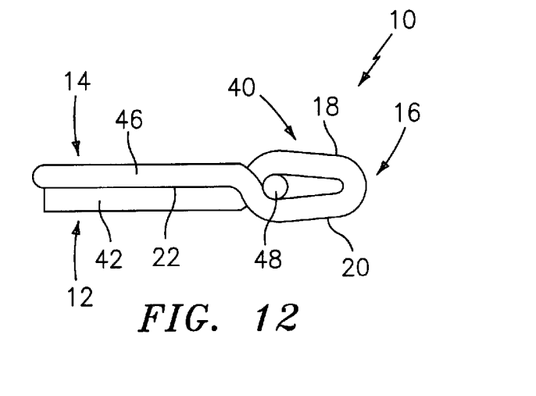
Figure 13:
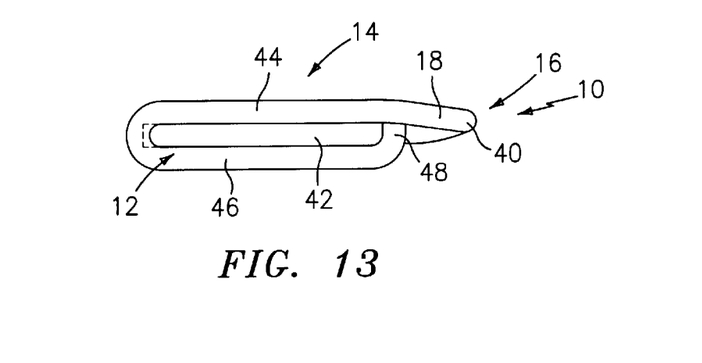

FIGS. 3 and 4 illustrate a side view of clip 10 in accordance with this embodiment in an open and a closed position respectively, and FIG. 5 illustrates a top view of clip 10 in accordance with this embodiment of the invention.

As shown, clip 10 is preferably provided from a single length of suitable material and preferably includes a U-shaped central portion 24 having a base 26 and two arms 28, 30 extending from base 26.

In connection with further description of clips 10 in accordance with the present invention, reference will be made to members extending in distal and proximal directions. By such references, distal refers to a direction from head portion 16 toward the tips of first and second legs 12, 14, and proximal refers to a direction generally from the tips of first and second leg 12, 14 toward head portion 16.

As shown in FIG. 2, arms 28, 30 extend generally proximally from base 26. Still referring to FIG. 2, clip 10 further includes a first segment 32 extending from a proximal end of arm 28 in a distal direction, preferably substantially parallel to arm 28, and past base 26 so as to define first leg 12 of clip 10. Clip 10 also includes a second segment 34 which extends from a proximal end of arm 30 in a distal direction, preferably also substantially parallel to arm 30, and past base 26 so as define second leg 14. As shown, first segment 32 and second segment 34 are preferably positioned in a crossing relationship as shown. The point where segments 32, 34 cross defines an inner most terminal end or proximal end 23 of tissue clamping zone 22. Also as shown, legs 12, 14 have proximal portions which are substantially adjacent in the open and closed positions at end 23 of zone 22.

In this embodiment, arms 28, 30 and/or proximal portions of first and second segments 32, 34, preferably both, define the deforming force receiving surfaces 18, 20 in accordance with the present invention.

Still referring to FIG. 2, in this embodiment, clip 10 preferably further includes a third segment 36 extending from a distal end of second segment 34 in a substantially proximal direction, and preferably substantially parallel to second segment 34, and a transverse segment 38 which may advantageously be positioned along and contacting base 26 so as to define a pivot point or fulcrum for relative pivot of first leg 12 relative to second leg 14 during a closing of clip 10. Transverse segment 38 advantageously helps to provide a clip which is very stable during application.

In accordance with the invention, clip 10 is applied through application of force F to surfaces 18, 20, which results in deforming of head portion 16 and pivotal closing of first and second legs 12, 14 to the position of FIG. 4. It should be noted that the magnitude of force F applied to surfaces 18, 20 is not transmitted directly to tissue T beyond the strength of material of clip 10. Rather, once clip 10 is closed, further application of force F to surfaces 18, 20 merely further compresses surfaces 18, 20, and does not further compress first leg 12 relative to second leg 14. Further, due to the structure of clip 10, tissue T in tissue clamping zone 22 is not positioned between inner edges of the portion of the clip defining force receiving surfaces 18, 20, and tissue T is therefore advantageously not subjected to direct application of clip deforming force. Still further, force to close the clip is applied to a zone other than the legs which typically are the widest portion of the clip. This allows the use of a smaller device for applying the clip which is particularly desirable.

Referring now to FIGS. 6–9, an embodiment of the invention is illustrated which is similar to that described in connection with FIGS. 2–5. In the embodiment of FIGS. 6–9, no transverse segment 38 is provided. This advantageously results in a cost savings for use of less materials, and through a simpler manufacturing process. Clip 10 of FIGS. 6–9 is suitable for use in accordance with the present invention, and is in all other respects identical to the clip of FIGS. 2–5.

Turning now to FIGS. 10–13, a further alternative embodiment of clip 10 in accordance with the present invention is illustrated. As shown, in this embodiment, clip 10 comprises a wire member having a substantially O-shaped central portion 40 defining head portion 16 and deforming force receiving surfaces 18, 20. Clip 10 in accordance with this embodiment further includes a first segment 42 and a second segment 44 which extend to define first and second legs 12, 14. In this embodiment, the central wire portion is provided in the O-shape as desired, and at a distal end of the O-shape the wire overlaps to allow first segment 42 to extend distally to define first leg 12, and to allow second segment 44 to extend distally so as to define second leg 14. As shown, first segment 42 crosses second segment 44 so as to define tissue clamping zone 22 between first leg 12 and second leg 14 such that application of clip deforming force to surfaces 18, 20 as shown by arrows F results in a pivot of first leg and second leg 12 and 14 to the closed position as desired all advantageously with surfaces 18, 20 defined outside of zone 22.

As shown in FIGS. 10–13, a third segment 46 may preferably be provided extending proximally from second segment 44 and preferably substantially parallel to second segment 44, and a transverse segment 48 may suitably be provided extending from a proximal end of third segment 46 and preferably substantially transverse to first and second segments 42, 44, most preferably where segments 42, 44 cross. Transverse segment 48 advantageously provides a pivot point or fulcrum around which legs, 12, 14 close, and helps to provide a stable structure and more reliable closing of legs 12, 14 as desired.

Referring now to FIGS. 14–17, a still further embodiment of the present invention is still illustrated. In this embodiment, clip 10 includes a substantially W-shaped central portion 50 which defines head portion 16 and deforming force receiving surfaces 18, 20 in accordance with the present invention. As shown, W-shaped central portion 50 preferably includes first and second segments 52, 54 which are joined to define a first apex 56 and second and third segments 58, 60 which extend from ends of first and second segments 52, 54 respectively so as to define the W-shape of the head portion of this embodiment. Third and fourth segments in this embodiment may be curved, if desired, so as to properly position legs 12, 14 in the open and closed positions as will be described below.

As shown, first segment 52 and third segment 58 define a second apex 66, and second segment 54 and fourth segment 60 define a third apex 68 which also form part of the W-shape of clip 10 of this embodiment. First apex 56 and second and third apexes 66, 68 are preferably positioned so as to face in opposite directions as shown. In this manner, apexes 56, 66 and 68 suitably define deforming force receiving surfaces, and clip 10 in accordance with the present invention is closed through application force F to first apex 56 and at least one of second and third apexes 66, 68 so as to substantially straighten first and second segments 52, 54 to the position illustrated in FIG. 16, thereby closing clip 10 as desired. In this embodiment, as in the other embodiments, deforming force receiving surfaces 18, 20 are advantageously defined outside of tissue clamping zone 22 such that application of force F to close clip 10 does not result in direct application of force to tissue T.

Still referring to FIGS. 14–17, clip 10 of this embodiment further may preferably include a fifth segment 62 preferably extending substantially distally from fourth segment 60 so as to define first leg 12, and a sixth segment 64 preferably extending substantially distally from fourth segment 60 so as define second leg 14.

Still referring to FIG. 14–17, clip 10 in accordance with this embodiment of the invention may suitably include a seventh segment 70 extending proximally from a distal end of sixth segment 64 as shown. It should be noted that this configuration, as with the configuration illustrated in FIGS. 2–13, advantageously result in a leg to space contact between the inner surfaces of first leg 12 and second leg 14 in tissue clamping zone 22 which further advantageously provides excellent occlusion of tissue T therebetween, not only through direct clamping, but through displacement as well.

Figure 14:
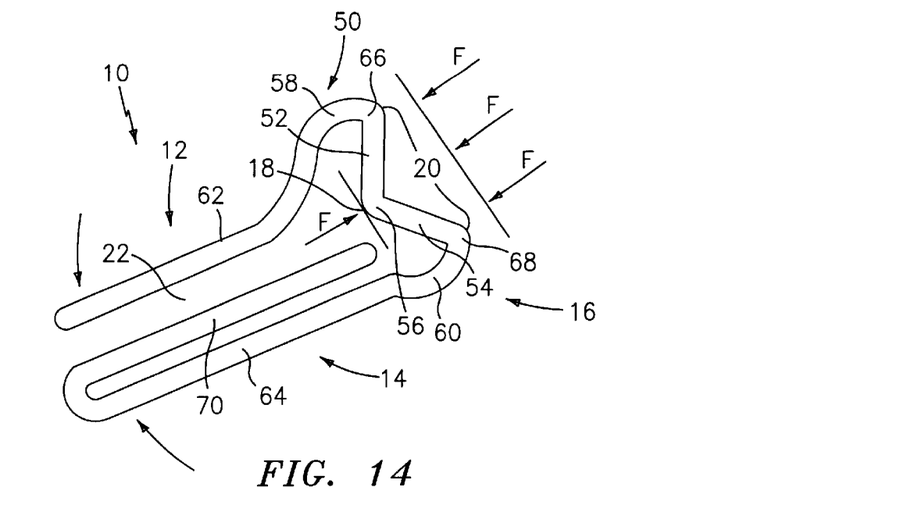
FIGS. 14–17 illustrate a clip in accordance with the present invention having a W-shaped head portion.
Figure 15:
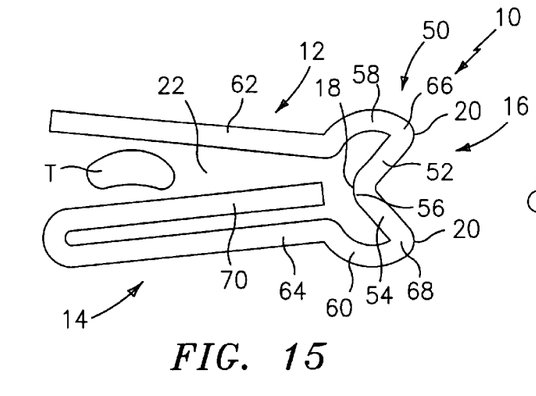
Figure 16:
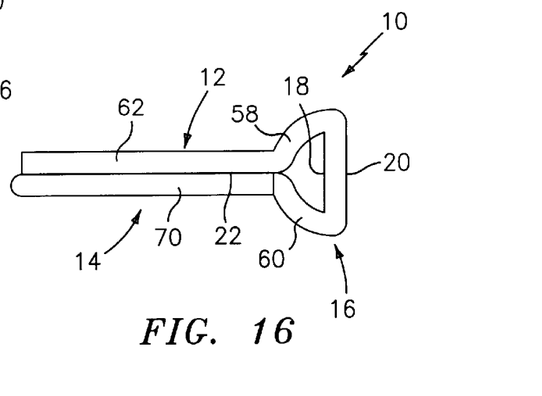
Figure 17:
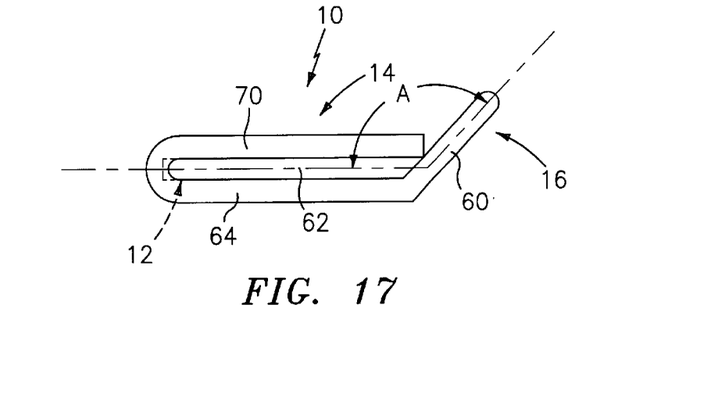

FIG. 17 shows a side view of the embodiment of FIG. 14, and further illustrates an additional advantageous feature of the present invention. As shown, head portion 16 of clip 10 of this embodiment is positioned at an angle A relative to first leg 12 and second leg 14 which is preferably greater than about 90° and less than about 180° such that head portion 16 can advantageously be used for positioning the clip within an applicator in a desirable application position wherein legs 12, 14 are articulated relative to the applier. In use, it is advantageous to be able to see legs 12, 14 and their positioning around tissue T before closing of clip 10. The described angling of head portion 16 relative to legs 12, 14 allows for the positioning of clip 10 against a vertical surface of an application, or against any other surface or component of a clip applicator, so as to position head portion 16 in a substantially vertical position with respect to the applicator, which advantageously cants or articulates legs 12, 14 to an angle with respect to the applicator to facilitate visibility. This feature of the present invention may advantageously be incorporated into the embodiments illustrated in FIGS. 2–13 as well as the embodiments of FIGS. 18–23 to be described below.

Figure 18:
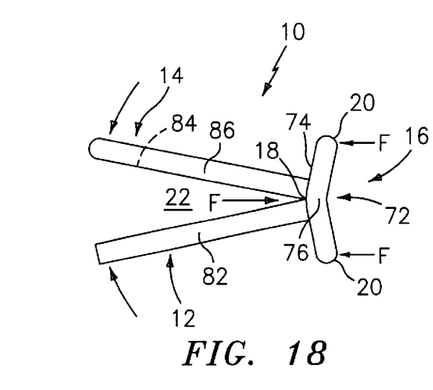
FIGS. 18–23 illustrate two embodiments of the present invention having a T-shaped head portion.
Figure 19:
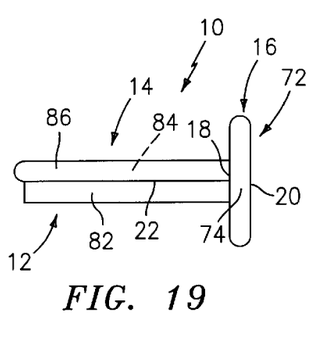
Figure 20:
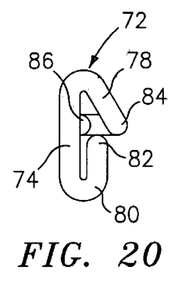

FIGS. 18–20 illustrate a further embodiment of clip 10 in accordance with the present invention wherein head portion 16 has a substantially T-shape. FIG. 18 shows a top view of a clip in accordance with this embodiment of the invention. Clip 10 includes a central portion 72 having a deformation segment 74 which in the open position has a substantially centrally located bend 76. Clip 10 further has curved segments 78, 80 which define a rough loop shape as best illustrated in FIG. 20, and segments 82, 84 extending from curved segment 78, 80 so as to define first leg 12 and second leg 14 respectively. In this embodiment, deformation segment 74 and curved segments 78, 80 define the deforming force receiving surfaces 18, 20, and clip 10 is positioned from the open position of FIG. 18 to the closed position of FIG. 19 through application of deforming force from a distal end to bend 76, and from a proximal end to distal edges of deformation segment 74. Application of such force advantageously straightens deformation segment 74 and pivots legs 12, 14 from the open position of FIG. 18 to the closed position of FIG. 19. As with other embodiments, deformation force receiving surfaces are advantageously located outside of tissue clamping zone 22.

In this embodiment, one or more additional segments 86 may suitably be positioned extending proximally from a distal end of segment or segments 82, 84 so as to provide for leg to space contact or closing of tissue T as described in connection with the embodiment of FIGS. 14–17 above. Further, in the embodiment of FIGS. 18–20, segments 82, 84 do not cross so that straightening of deformation segment 74 results in closing of legs as desired.

Figure 21:
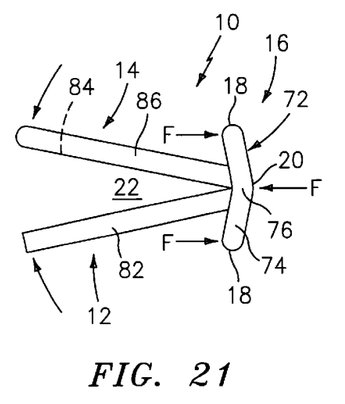
Figure 22:
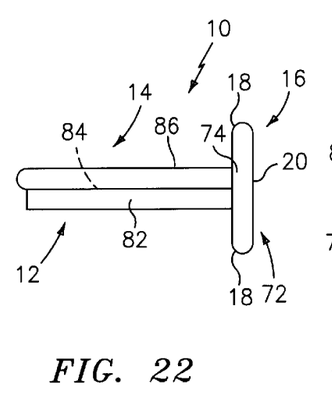
Figure 23:
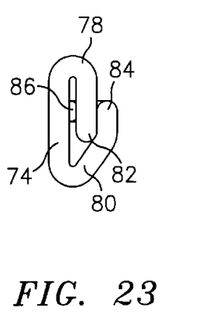

Referring now to FIGS. 21–23, an embodiment similar to that of FIGS. 18–20 is described. In this embodiment, however, segments 82, 84 do cross, and deformation segment 74 is configured so as to have bend 76 facing proximally. Thus, in this configuration, central portion 72 defines deformation force receiving surfaces 18, 20 at proximally facing bend 76 and distal-most portions of deformation segment 74. Application of force F to these points serves to straighten deformation segment 74 to the position of FIG. 22, thereby advantageously closing legs 12, 14 as desired. One or more additional segments 86 may be incorporated in this embodiment as well, so as to provide enhanced clamping or occlusion of tissue T as desired.

Clip 10 in accordance with any of the embodiments of the present invention is preferably provided from a material such as implantable stainless steel, titanium, tantalum and the like, which material is preferably selected so as to be suitably deformable and to have a yield strength sufficiently low that over-application of force to surfaces 18, 20 once clip 10 is closed will result in yielding of material of clip 10 rather than transmittal of excessive force to tissue T within tissue clamping zone 22. This is particularly advantageous as compared to the conventional clip of FIG. 1 wherein all force applied to clip 10 is directly transmitted to tissue T in the tissue clamping zone regardless of the material from which the clip is made.

Figure 24:
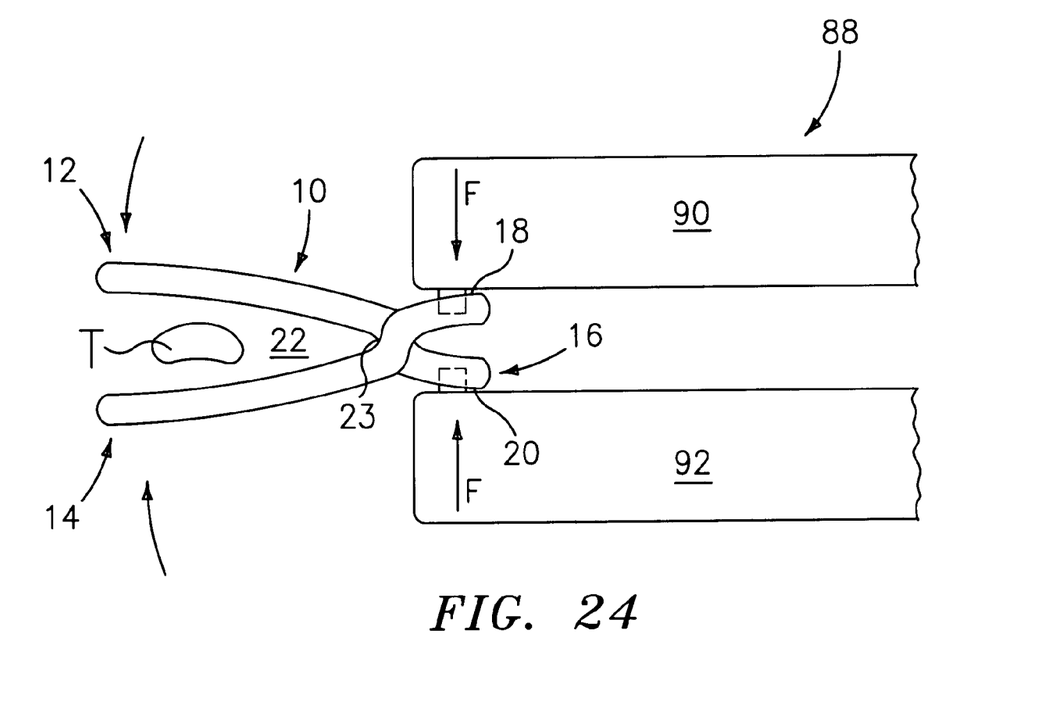
FIG. 24 illustrates a method for applying a U-clip in accordance with the present invention.

Referring now to FIG. 24, a method for applying a clip 10 in accordance with the present invention is illustrated. In use, clip 10 is preferably positioned with force receiving surfaces 18, 20 engaged by an applier 88 which may suitably have force applying jaws 90, 92. Clip 10 so positioned in an applier 88 is then positioned around tissue T, with tissue T in tissue clamping zone 22. Jaws 90, 92 are then closed as illustrated by arrows F so as to apply deforming force to surfaces 18, 20, advantageously outside of tissue clamping zone 22. Such force results in deformation of head portion 16, specifically in closing of the U-shaped central portion 24 in the illustrated embodiment, so as to pivot legs 12, 14 to a closed position for clamping and occluding tissue T as desired. It should readily be apparent that once clip 10 is closed, additional force applied through jaws 90, 92 is not transmitted directly to tissue T.

It should be noted that the applier illustrated in FIG. 24 is a schematic illustration of one basic form of applier, and that numerous other structures and configurations could be used for applying clips 10 in accordance with the present invention.

It should also be appreciated that, although clips 10 are referred to herein as having a U, O, W or T-shape, other shaped head portions could be provided which would perform well within the scope of the present invention so as to define force receiving surfaces outside of a tissue clamping zone as desired.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed:

1. A ligating clip, comprising:
   a first leg and a second leg defining therebetween a tissue clamping zone; and
   a deformable head portion connecting said first leg and said second leg and deformable from an open position wherein said first leg and said second leg are spaced to receive tissue to a closed position wherein said first leg and said second leg are closed to clamp tissue,
   wherein said deformable head portion defines deforming force receiving surfaces which are outside said tissue clamping zone, wherein said first leg and said second leg meet at a pivot point defining an inner most terminal end of said tissue clamping zone, and wherein said deforming force receiving portions extend from said pivot point away from said tissue clamping zone.

2. A clip according to claim 1, wherein said clip comprises a single deformable wire having a central portion defining said head portion and said deforming force receiving surfaces, a first segment extending from said central portion to define said first leg and a second segment extending from said central portion to define said second leg.

3. A clip according to claim 2, wherein said first leg and said second leg having proximal ends where said first segment and said second segment extend from said central portion, and wherein said proximal ends are substantially adjacent when said clip is in said open position.

4. A clip according to claim 3, wherein said first segment crosses said second segment so as to define a point for pivotal closing of said first leg relative to said second leg.

5. A clip according to claim 4, wherein said wire further comprises a third segment extending proximally from a distal end of one leg of said first leg and said second leg and substantially parallel to said one leg to said point, and a transverse segment extending substantially transverse along said point so as to define a pivot point for said first leg relative to said second leg.

6. A ligating clip, comprising:

a first leg and a second leg defining therebetween a tissue clamping zone; and a deformable head portion connecting said first leg and said second leg and deformable from an open position wherein said first leg and said second leg are spaced to receive tissue to a closed position wherein said first leg and said second leg are closed to clamp tissue, wherein said deformable head portion defines deforming force receiving surfaces which are outside said tissue clamping zone, wherein said clip comprises a single deformable wire having a U-shaped central portion having a base and two arms extending proximally from said base, said wire further having a first segment extending from a first arm of said two arms substantially parallel to said first arm in a distal direction past said base to define said first leg, and said wire further having a second segment extending from a second arm of said two arms substantially parallel to said second arm in a distal direction past said base to define said second leg, said second segment crossing said first segment at a point to define a proximal end of said tissue clamping zone and so as to define proximal portions of said first segment and said second segment which are proximal of said point, at least one of said two arms and said proximal portions defining said deforming force receiving surfaces.

7. A clip according to claim 6, wherein said wire further comprises a third segment extending proximally from a distal end of one leg of said first leg and said second leg and substantially parallel to said one leg to said point, and a transverse segment extending substantially transverse along said point so as to define a pivot point for said first leg relative to said second leg.

8. A ligating clip, comprising:

a first leg and a second leg defining therebetween a tissue clamping zone; and a deformable head portion connecting said first leg and said second leg and deformable from an open position wherein said first leg and said second leg are spaced to receive tissue to a closed position wherein said first leg and said second leg are closed to clamp tissue, wherein said deformable head portion defines deforming force receiving surfaces which are outside said tissue clamping zone, wherein said clip comprises a single deformable wire having a central portion defining said head portion and said deforming force receiving surfaces, a first segment extending from said central portion to define said first leg and a second segment extending from said central portion to define said second leg, and wherein said first leg and said second leg have proximal ends where said first segment and said second segment extend from said central portion, and wherein said proximal ends are substantially adjacent when said clip is in said open position.

9. A ligating clip, comprising:

a first leg and a second leg defining therebetween a tissue clamping zone; and a deformable head portion connecting said first leg and said second leg and deformable from an open position wherein said first leg and said second leg are spaced to receive tissue to a closed position wherein said first leg and said second leg are closed to clamp tissue, wherein said deformable head portion defines deforming force receiving surfaces which are outside said tissue clamping zone, wherein said clip comprises a single deformable wire having a central portion defining said head portion and said deforming force receiving surfaces, a first segment extending from said central portion to define said first leg and a second segment extending from said central portion to define said second leg, and wherein said first segment crosses said second segment so as to define a point for pivotal closing of said first leg relative to said second leg.

10. A ligating clip, comprising:

a first leg and a second leg defining therebetween a tissue clamping zone; and a deformable head portion connecting said first leg and said second leg and deformable from an open position wherein said first leg and said second leg are spaced to receive tissue to a closed position wherein said first leg and said second leg are closed to clamp tissue, wherein said deformable head portion comprises force receiving members defining deforming force receiving surfaces, wherein said force receiving members and said deforming force receiving surfaces are spaced from and outside of said tissue clamping zone, whereby said tissue positioned between said first and second legs is prevented from entering a position between said force receiving members.

11. A clip according to claim 10, wherein said clip comprises a single deformable wire having an O-shaped central portion defining said head portion and said deforming force receiving surfaces, a first segment extending from said central portion and defining said first leg and a second segment extending from said central portion and defining said second leg.

12. A clip according to claim 11, wherein said first segment crosses said second segment so as to define a point for pivotal closing of said first leg relative to said second leg.

13. A clip according to claim 12, wherein said wire further comprises a third segment extending proximally from a distal end of one leg of said first leg and said second leg and substantially parallel to said one leg to said point, and a transverse segment extending substantially transverse along said point so as to define a pivot point for said first leg relative to said second leg.

* * * * *